US005786213A

United States Patent [19]

Singh et al.

[11] Patent Number: 5,786,213
[45] Date of Patent: Jul. 28, 1998

[54] INHIBITION OF ENDOGENOUS GASTRIN EXPRESSION FOR TREATMENT OF COLORECTAL CANCER

[75] Inventors: Pomila Singh, Galveston; Thomas G. Wood, Houston, both of Tex.

[73] Assignee: Board of Regents, The University of Texas System, Austin, Tex.

[21] Appl. No.: 634,546

[22] Filed: Apr. 18, 1996

[51] Int. Cl.$^6$ ..................................................... C12N 5/00
[52] U.S. Cl. .................. 435/320.1; 435/60.1; 435/172.3; 435/325; 514/44; 514/2; 424/93.21; 536/23.1; 536/22.3; 536/24.3
[58] Field of Search ........................... 424/93.21; 514/44, 514/2; 536/22.3, 24.1, 24.3, 23.1; 935/77.78, 325, 69.1, 172.3

[56] References Cited

U.S. PATENT DOCUMENTS 5,190,931  3/1993  Inouye ......................................... 435/91
5,585,479  12/1996  Hoke et al. ............................. 536/24.5

OTHER PUBLICATIONS

Ito et al., "Structural analysis of the gene encoding human gastrin: The large intron contains an Alu sequence," *Proc. Natl. Acad. Sci. USA,* 81:4662–66, 1984.

Baldwin et al., "PCR Cloning and Sequence of Gastrin mRNA from Carcinoma Cell Lines," *Biochemical and Biophysical Research Communications,* 170(2):691–697, Jul. 1990.

Chicone et al., "The Presence of a 33—40 Kda Gastrin Binding Protein on Human and Mouse Colon Cancer," *Biochemical and Biophysical Research Communications,* 164(1):512–519, Oct. 1989.

Finley et al., "Expression of the Gastrin Gene in the Normal Human Colon and Colorectal Adenocarcinoma," *Cancer Research,* 53:2919–2926, Jun. 1993.

Hoosein et al., "Antiproliferative Effects of Gastrin Receptor Antagonists and Antibodies to Gastrin on Human Colon Carcinoma Cell Lines," *Cancer Research,* 48:7179–7183, Dec. 1989.

Imdahl et al., "Expression of Gastrin, Gastrin/CCK-B-and Gastrin/CCK-C Receptors in Human Colorectal Carcinomas," *Gastroenterology,* 108(4):A484.

Kato et al, "Molecular Cloning of Human Gastrin Precursor cDNA," *Gene,* 26:53–57, 1983.

Lebovitz et al., "The Role of Gastrin in Colorectal Cancer Cell Lines," *Proceedings of the American Association for Cancer Research,* 35:42, Abstract No. No. 248, Mar. 1994.

Rehfeld and Hilsted, "Gastrin and Cancer," *Advances in Clinical Chemistry,* 29:239–262, 1992.

Singh et al., "Novel Gastrin Receptors Mediate Mitogenic Effects of Gastrin and Processing Intermediates of Gastrin on Swiss 3T3 Fibroblasts," *The Journal of Biological Chemistry,* 270(15):8429–8438, Apr. 1995.

Singh et al., "Anti–Tumorigenic Effects of a Recombinant Retrovirus Over–Expressing Antisense Gastrin cDNA on a Human Colon Cancer Cell Line," *Annual Meeting of American Gastroenterological Association and American Association for the Study of Liver Diseases,* May 19–22, 1996.

Singh et al., "Incomplete Processing of Progastrin Expressed by Human Colon Cancer Cells: Role of Noncarboxyamidated Gastrins," *The American Physiological Society,* G459–G468, 1994.

Upp et al., "Clinical Significance of Gastrin Receptors in Human Colon Cancers," *Cancer Research,* 49:488–492, Jan. 1989.

Xu et al., "Gastrin Gene Expression in Human Colon Cancer Cells Measured by a Simple Competitive PCR Method," *Life Sciences,* 54(10):671–678, 1994.

Ledley, "Somatic Gene Therapy in Gastroenterology: Approaches and Applications" *Journal of Pediatric Gastroenterology and Nutrition,* 14:328–337, 1992.

International Search Report for PCT/US97/06528, mailed Jun. 24, 1997.

Gilboa. Seminars In Oncology, vol. 23, 1 : 101–107, 1996.

Mashangelo et al., Seminars In Oncology, vol. 23, 1 : 4–21, 1996.

Jeun, Scientific American, Jul. 1994, pp. 58–65.

Herrman. J. Mol. Med. Today. 1995, 73:157–163.

Ronald Crystal. Science. 1995, 270:404–409.

Coghlan. New Scientist. 1995, vol. 148, pp. 14 and 15, 1995.

Wagner et al. Nature. 1994, vol. 372:333–335.

Gura. Science. 1995, 270:575–577.

Plenat. J. Mol. Med. Today. 1996, vol. 2, No. 6:250–257.

Bold et al. Surgery. 1994, 116/2:189–95.

Kato et al. Gene. 1983, 2:53–57.

*Primary Examiner*—Christopher S. F. Low
*Assistant Examiner*—Dave Trong Nguyen
*Attorney, Agent, or Firm*—Arnold White & Durkee

[57] ABSTRACT

The present invention discloses is for the treatment of colon cancer. The expression of gastrin by colon cancers is inhibited by the use of antisense gastrin expression. Methods are disclosed for the preparation of expression constructs and the use of such constructs to inhibit colon cancer growth.

9 Claims, 4 Drawing Sheets

1 2 3 4 5

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 613 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATGCAGCGAC TATGTGTGTA TGTGCTGATC TTTGCACTGG CTCTGGCCGC CTTCTCTGAA     60
GCTTCTTGGA AGCCCCGCTC CCAGCAGCCA GATGCACCCT TAGGTACAGG GGCCAACAGG    120
GACCTGGAGC TACCCTGGCT GGAGCAGCAG GGCCCAGCCT CTCATCATCG AAGGCAGCTG    180
GGACCCCAGG GTCCCCCACA CCTCGTGGCA GGTAGGAGCT GCTGACTGCC CTGCTTGCCT    240
CACTTGGCCA GGTTTGGCCA AGGTCTCCCC AGACTGGCTC TGACTTCAGT TCCTGGAAGG    300
TAGGCATCCT TCCCCCATTC TCGCCTCTCT CACCTCCTCA GACCCGTCCA AGAAGCAGGG    360
ACCATGGCTG GAGGAAGAAG AAGAAGCCTA TGGATGGATG GACTTCGGCC GCCGCAGTGC    420
TGAGGATGAG AACTAACAAT CCTAGAACCA AGCTTCAGAG CCTAGCCACC TCCCACCCCA    480
CTCCAGCCCT GTCCCCTGAA AAACTGATCA AAAATAAACT AGTTTCCAGT GGATCAATGG    540
ACTGTGTCAG TGTTGTAGGG CAGAGGAGGG GGACTCATCT GGGGGTGAAG TTGTGGCAGG    600
GAGAAGAGCT GAG                                                      613
```

( 2 ) INFORMATION FOR SEQ ID NO:2:

( i ) SEQUENCE CHARACTERISTICS:
        ( A ) LENGTH: 70 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met Gln Arg Leu Cys Val Tyr Val Leu Ile Phe Ala Leu Ala Leu Ala
 1               5                  10                  15
Ala Phe Ser Glu Ala Ser Trp Lys Pro Arg Ser Gln Gln Pro Asp Ala
                20                  25                  30
Pro Leu Gly Thr Gly Ala Asn Arg Asp Leu Glu Leu Pro Trp Leu Glu
                35                  40                  45
Gln Gln Gly Pro Ala Ser His His Arg Arg Gln Leu Gly Pro Gln Gly
                50                  55                  60
Pro Pro His Leu Val Ala
65                  70
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AGGCCCAGCC GTGGCACCAC A                                              21
```

( 2 ) INFORMATION FOR SEQ ID NO:4:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

TGGCTAGGCT CTGAAGCTTG GTT                           23

( 2 ) INFORMATION FOR SEQ ID NO:5:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

CCTGGAGACG CCATCCACGC T                             21

( 2 ) INFORMATION FOR SEQ ID NO:6:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

GTGTATGTGC TGATCTTTGC ACTG                          24

( 2 ) INFORMATION FOR SEQ ID NO:7:

( i ) SEQUENCE CHARACTERISTICS:
      ( A ) LENGTH: 74 amino acids
      ( B ) TYPE: amino acid
      ( C ) STRANDEDNESS:
      ( D ) TOPOLOGY: linear ( x i ) SEQUENCE DESCRIPTION: SEQ ID NO:7:

```
Ser Trp Lys Pro Arg Ser Gln Gln Pro Asp Ala Pro Leu Gly Thr Gly
 1               5                  10                  15

Ala Asn Arg Asp Leu Glu Leu Pro Trp Leu Glu Gln Gln Gly Pro Ala
             20                  25                  30

Ser His His Arg Arg Gln Leu Gly Pro Gln Gly Pro Pro His Leu Val
         35                  40                  45

Ala Asp Pro Ser Lys Lys Gln Gly Pro Trp Leu Glu Glu Glu Glu Glu
     50                  55                  60

Ala Tyr Gly Trp Met Asp Phe Gly Arg Arg
 65              70
```

( 2 ) INFORMATION FOR SEQ ID NO:8:

( i ) SEQUENCE CHARACTERISTICS:
      ( A ) LENGTH: 35 amino acids
      ( B ) TYPE: amino acid
      ( C ) STRANDEDNESS:
      ( D ) TOPOLOGY: linear ( x i ) SEQUENCE DESCRIPTION: SEQ ID NO:8:

```
Gln Leu Gly Pro Gln Gly Pro Pro His Leu Val Ala Asp Pro Ser Lys
 1               5                  10                  15

Lys Gln Gly Pro Trp Leu Glu Glu Glu Glu Glu Ala Tyr Gly Trp Met
             20                  25                  30
```

Asp Phe Gly
        35

( 2 ) INFORMATION FOR SEQ ID NO:9:

( i ) SEQUENCE CHARACTERISTICS:
        ( A ) LENGTH: 34 amino acids
        ( B ) TYPE: amino acid
        ( C ) STRANDEDNESS:
        ( D ) TOPOLOGY: linear ( x i ) SEQUENCE DESCRIPTION: SEQ ID NO:9:

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
                20                  25                  30

Asp Phe ( 2 ) INFORMATION FOR SEQ ID NO:10:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( x i ) SEQUENCE DESCRIPTION: SEQ ID NO:10:

Gln Gly Pro Trp Leu Glu Glu Glu Glu Ala Tyr Gly Trp Met Asp
1               5                   10                  15

Phe Gly ( 2 ) INFORMATION FOR SEQ ID NO:11:

( i ) SEQUENCE CHARACTERISTICS:
        ( A ) LENGTH: 35 amino acids
        ( B ) TYPE: amino acid
        ( C ) STRANDEDNESS:
        ( D ) TOPOLOGY: linear ( x i ) SEQUENCE DESCRIPTION: SEQ ID NO:11:

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
                20                  25                  30

Ser His His
        35

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( x i ) SEQUENCE DESCRIPTION: SEQ ID NO:12:

Pro Ser Lys Lys Gln Gly Pro Trp Leu Glu Glu Glu Glu Ala Tyr
1               5                   10                  15

Gly Trp Met Asp Phe
            20

INHIBITION OF ENDOGENOUS GASTRIN EXPRESSION FOR TREATMENT OF COLORECTAL CANCER

The US government owns rights in the present invention pursuant to grant numbers CA60087 from the National Institutes of Health.

BACKGROUND OF THE INVENTION

1. Field of the Invention

The present invention relates generally to the treatment of colon cancers. More particularly, it concerns the use of antisense gastrin expression to reduce colon cancer growth.

2. Description of Related Art

Colorectal cancers are among the most common cancers in men and women in the U.S. and are one of the leading causes of death (Steel, 1994). Other than surgical resection no other systemic or adjuvant therapy is available. Vogelstein and colleagues have described the sequence of genetic events that appear to be associated with the multistep process of colon cancer development in humans (Fearon and Vogelstein, 1990). An understanding of the molecular genetics of carcinogenesis, however, has not led to preventative or therapeutic measures. It can be expected that advances in molecular genetics will lead to better risk assessment and early diagnosis but colorectal cancers will remain a deadly disease for a majority of patients due to the lack of an adjuvant therapy. Adjuvant or systemic treatments are likely to arise from a better understanding of the autocrine factors responsible for the continued proliferation of cancer cells.

Endogenous gastrins and exogenous gastrins (other than tetragastrin) seem to promote the growth of established colon cancers in mice (Singh, et cl., 1986; Singh, et al., 1987; et al., 1984; Smith and Solomon, 1988; Singih, el cit., 1990; Rehfeld and van Solinge, 1994) and promote carcinogen induced colon cancers in rats (Williamson et al., 1978; Karlin et al., 1985; Lamoste and Willems; 1988). Recent studies of Montag et al (1993) further support a possible co-carcinogenic role of gastrin in the initiation of tumors.

Many colon cancer cells express and secrete gastrin gene products (Dai et al., 1992; Kochinan et al., 1992; Finley et al., 1993; Van Solinge et al., 1993; Xu et al., 1994; Singh et al., 1994a; Hoosein et al., 1988; Hoosein et al., 1990) and bind gastrin-like peptides (Singh et al., 1986; Singh et al., 1987; Weinstock and Baldwin, 1988; Watson and Steele, 1994; Upp et al., 1989; Singh et al., 1985). In previous reports gastrin antibodies were either reported to inhibit (Hoosein et al, 1988; Hoosein et al, 1990) the growth of colon cancer cell lines in vitro.

However other investigators have had inconclusive results with colon cancer cell lines. A number of studies testing the effects of gastrin on cell proliferation of cancer cells have been performed (Sirinek et al., 1985; Kusyk et al., 1986; Watson et al., 1989). The results have varied widely. In one study, four different human cancer cell lines were tested for growth stimulation by pentagastrin and only one showed growth stimulation (Eggstein et al., 199 1). Similarly in majority of the studies conducted to-date, mitogenic effects of gastrin have been demonstrated only on a very small percentage of colon cancer cell lines in vitro (Hoosein et al., 1988; Hoosein et al, 1990; Shrink et al, 1985; Kusyk et al, 1986; Guo et al, 1990; Ishizuka et al, 1994).

Since only a small percentage of established human colon cancer cell lines demonstrated a growth response to exogenous gastrins, investigators in this field came to believe that gastrin probably did not play a significant role in the growth of colon cancers. The recent discovery that human colon cancer cell lines and primary human colon cancers express the gastrin gene has sparked a renewed interest in a possible autocrine role of gastrin-like peptides in colon cancers. However, significant skepticism remains in the field, to date, regarding the importance of gastrin gene expression to the continued growth and tumorogenicity of colon cancers.

Thus, to-date, no systemic or adjuvant therapies have been developed for colon cancers, based on the knowledge that a significant percentage of human colon cancers express the gastrin gene. In fact, no adjuvant or systemic therapy has been developed for colon cancers that is based on the knowledge of the expression of other growth factors such as TFGFα or IGF.-11, since none of the growth factors demonstrate a significant growth effect on majority of the colon cancer cell lines in culture.

At the present time the only systemic treatment available for colon cancer is chemotherapy. However, chemotherapy has not proven to be very effective for the treatment of colon cancers for several reasons, the most important of which is the fact that colon cancers express high levels of the MDR gene (that codes for multi-drug resistance gene products). The MDR gene products actively transport the toxic substances out of the cell before the chemotherapeutic agents can damage the DNA machinery of the cell. These toxic substances harm the normal cell populations more than they harm the colon cancer cells for the above reasons.

There is no effective systemic treatment for treating colon cancers other than surgically removing the cancers. In the case of several other cancers, including breast cancers, the knowledge of growth promoting factors (such as EGF, estradiol, IGF-11) that appear to be expressed or effect the growth of the cancer cells, has been translated for treatment purposes. But in the case of colon cancers this knowledge has not been applied and therefore the treatment outcome for colon cancers remains bleak.

Antisense RNA technology has been developed as an approach to inhibiting gene expression, particularly oncogene expression. An "antisense" RNA molecule is one which contains the complement of, and can therefore hybridize with, protein-encoding RNAs of the cell. It is believed that the hybridization of antisense RNA to its cellular RNA complement can prevent expression of the cellular RNA, perhaps by limiting its translatability. While various studies have involved the processing of RNA or direct introduction of antisense RNA oligonucleotides to cells for the inhibition of gene expression (Brown, et al., 1989; Wickstrom, et al., 1988; Smith, et al., 1986; Buvoli, et al., 1987), the more common means of cellular introduction of antisense RNAs has been through the construction of recombinant vectors which will express antisense RNA once the vector is introduced into the cell.

A principle application of antisense RNA technology has been in connection with attempts to affect the expression of specific genes. For example, Delauney, et al. have reported the use antisense transcripts to inhibit gene expression in transgenic plants (Delauney, et al., 1988). These authors report the down-regulation of chloramphenicol acetyl transferase activity in tobacco plants transformed with CAT sequences through the application of antisense technology.

Antisense technology has also been applied in attempts to inhibit the expression of various oncogenes. For example, Kasid, et al., 1989, report the preparation of recombinant vector construct employing Craf-1 cDNA fragments in an antisense orientation, brought under the control of an adenovirus 2 late promoter. These authors report that the introduction of this recombinant construct into a human squamous carcinoma resulted in a greatly reduced tumorigenic potential relative to cells transfected faith control sense transfectants. Similarly, Prochownik, et al., 1988, have reported the use of Cmiyc antisense constructs to accelerate differentiation and inhibit $G_1$ progression in Friend Murine Erythroleukemia cells. In contrast, Khokha, et al., 1989, discloses the use of antisense RNAs to confer oncogenicity on 3T3 cells, through the use of antisense RNA to reduce murine tissue inhibitor or metalloproteinases levels.

Antisense methodology takes advantage of the fact that nucleic acids tend to pair with "complementary" sequences. By complementary, it is meant that polynucleotides are those which are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Throughout this application, the term "expression vector or construct" is meant to include any type of genetic construct containing a nucleic acid coding for a gene product in which part or all of the nucleic acid encoding sequence is capable of being transcribed. The transcript may be translated into a protein but it need not be. Thus, in certain embodiments, expression includes both transcription of a gene and translation of mRNA into a gene product. In other embodiments, expression only includes transcription of the nucleic acid encoding a gene of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter is used to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various instances, the human cytomegalovirus (CMV) immediate early gene promoter, the SV40 early promoter and the Rous sarcoma virus long terminal repeat can be used to obtain high-level expression of the gene of interest. The use of other viral or mammalian cellular or bacterial phage promoters which are well-known in the art to achieve expression of a gene of interest is contemplated as well, provided that the levels of expression are sufficient for a given purpose.

By employing a promoter with well-known properties, the level and pattern of expression of the gene product following transfection can be optimized. Further, selection of a promoter that is regulated in response to specific physiologic signals can permit inducible expression of the gene product. Several elements/promoters which may be employed, in the context of the present invention, to regulate the expression of the gene of interest are listed below. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Viral promoters, cellular promoters/enhancers and inducible promoters/enhancers that could be used in combination with the nucleic acid encoding a gene of interest in an expression construct. Some examples of enhancers include Immunoglobulin Heavy Chain; Immunoglobulin Light Chain; T-Cell Receptor; HLA DQ a and DQ b b-Interferon; Interleukin-2; Interleukin-2 Receptor; Gibbon Ape Leukemia Virus; MHC Class II 5 or HLA-DRa; b-Actin; Muscle Creatine Kinase; Prealbumin (Transthyretin); Elastase I; Metallothionein; Collagenase, Albumin Gene; a-Fetoprotein; a-Globin; b-Globin; c-fos; c-HA-ras; Insulin Neural Cell Adhesion Molecule (NCAM); al-Antitrypsin; H2B (TH2B) Histone; Mouse or Type I Collagen; Glucose-Regulated Proteins (GRP94 and GRP78); Rat Growth Hormone; Human Serum Amyloid A (SAA); Troponin I (TN I); Platelet-Derived Growth Factor; Duchenne Muscular Dystrophy; SV40 or CMV; Polyoma; Retroviruses; Papilloma Virus; Hepatitis B Virus; Human Immunodeficiency Virus. Inducers such as phorbol ester (TFA) heavy metals; glucocorticoids; poly (rl)X; poly(rc); Ela; $H_2O_2$;IL 1; Interferon, Newcastle Disease Virus; A23187; IL-6; Serum; SV40 Large T Antigen; FMA; thyroid Hormone; could be used. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In certain instances, the expression construct will comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal et al., 1986: Temin, 1986). The first viruses used as gene vectors were DNA viruses including the papoviruses (simian virus 40, bovine papilloma virus, and polyoma) (Ridgeway, 1988; Baichwal et al., 1986) and adenoviruses (Ridgeway, 1988; Baichwal et al., 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Also often another element of the expression cassette is a terminator. These elements can serve to enhance message levels and to minimize read through from the cassette into other sequences.

It is understood in the art that to bring a coding sequence under the control of a promoter, or operatively linking a sequence to a promoter, one positions the 5' end of the transcription initiation site of the transcriptional reading frame of the protein between about 1and about 50 nucleotides "downstream" of (i.e., 3' of) the chosen promoter. In addition, where eukaryotic expression is contemplated, one will also typically desire to incorporate into the transcriptional unit which includes the cotransporter protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

The above background references are part of the present invention insofar as they are applicable to the invention described herein.

Hence there are no effective and specific ways of treating or diminishing the growth of colorectal cancer to date.

SUMMARY OF THE INVENTION

Therefore, it is an object of the present invention to provide improved methods for the treatment of colorectal cancer.

In fulfilling this object, there is provided a method for inhibiting the growth of gastrin expressing colon cancer cells comprising reducing the gastrin expression of the colon cancer cells by inducing the production of inhibitory antisense polynucleotides in cancer cells.

In certain embodiments of the present invention there are provides methods for treating colon cancer in a patient comprising the steps of (a) providing an expression construct comprising a promoter functional in eukaryotic cells and a polynucleotide encoding a gastrin gene, wherein the polynucleotide is positioned antisense to and under the control of the promoter; and (b) contacting the expression construct with the colon cancer in vivo to produce transformed colon cancer cells deficient in gastrin production.

The colon cancer may be a human colon cancer. The expression construct preferably is a viral vector, such as a retroviral vector, an adenoviral vector and an adeno-associated viral vector, with a retroviral vector being most preferred.

The polynucleotide may encode gastrin, preprogastrin, pregastrin, gly-gastrin amidated gastrin with gastrin being most preferred. The promoters regions to be used of the present invention are known to those of skill in the art for example, the polynucleotide sequence may be under the control of CMV, LTR or SV40.

The method of contracting the expression construct with the colon cancer cells may comprise intratumoral injection, osmotic pump delivery or targeted liposomal delivery. Of course these methods would have to optimized for the individual case using procedures known to those of skill in the art.

Continuous perfusion of the expression construct also is contemplated. The amount of construct delivered in continuous perfusion into the tumor site will be determined from the amount delivered via injections so as to approximate the same total dosage over a given time period, although somewhat greater total dosages may be achieved using continuous perfusion.

Also disclosed are compositions for treating colon cancer comprising a poly nucleotide sequence encoding a gastrin gene expression construct wherein the gastrin gene is positioned antisense to and under the control of promoter functional in eukaryotic cells. The composition for treating colon cancer may comprise a polynucleotide sequence of SEQ ID NO: 1positioned antisense to and under the control of a promoter.

A more preferred polynucleotide sequence comprises 21 to 24 base pairs of SEQ ID NO: 1. Another preferred sequence comprises sequences of SEQ ID NO: 3. Another preferred sequence is a contiguous oligonucleotide sequence comprising SEQ ID NO: 4 yet another preferred sequence is a contiguous oligonucleotide sequence of SEQ ID NO: 7. Of course it is understood that any contiguous sequence comprising 5, 6, 7, 8, 9, 10, 15, or 20 base pairs from SEQ ID NO: 3, SEQ ID NO: 4 and SEQ ID NO: 7 may also be used in the practise of the present invention.

Another embodiment of the present invention provides kits comprising in suitable container means, a polynucleotide encoding a gastrin expression construct wherein the gastrin gene is positioned under the control of a promoter functional in eukaryotic cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The relative concentrations of gastrin mRNA in each cell line were additionally quantitated by competitive RT-PCR using gastrin gDNA as an internal control as described previously (Xu et al., 1994; Singh et al., 1994a) and the data are presented in the text. Lanes 1–5=Mw markers, Colo-205A, HCT-116, Colo-320 and HCT-116 samples without RT, respectively.

Figure 2A:
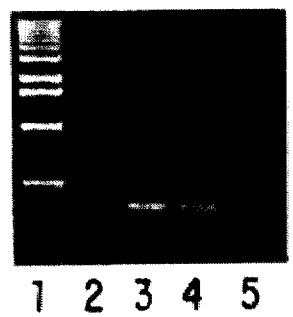
FIG. 2A: The human colon cancer cell lines Colo-205A (sub-cloned from Colo-205 [ATCCJ], Colo-320 (ATCC) and HCT-116 were analyzed for relative concentrations of gastrin mRNA by RF-PCR (reverse transcriptase-polymerase chain reaction) using 2 µg of total RNA in the reaction (Rx) mixture, as published previously (Xu et al., 1994; Singh et al., 1994a). Ethidium bromide staining of PCR products (target size 417 bp) of a representative Rx, using primers $HG_4$ (5'AGGCCCAGCCGTGGCACCACA3'; SEQ ID NO: 3) and $HG_5$ (5'TGGCTAGGCTCGAAGCTTGGTT3'; SEQ ID NO: 4) is shown.
Figure 2B:
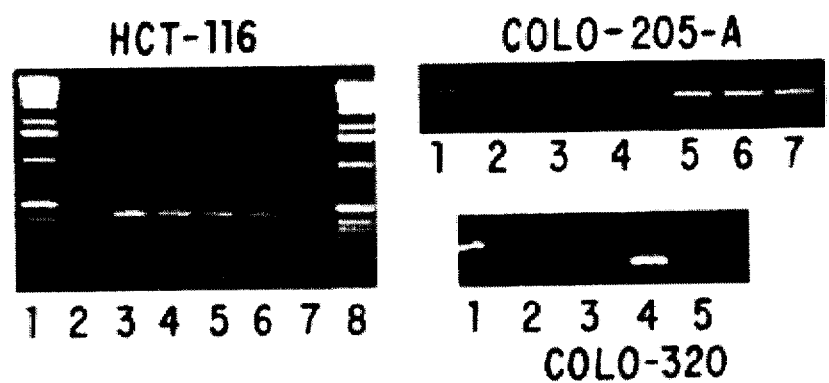

FIG. 2B: Each cell line was transfected with C- or LNC-G-AS vector DNA and G418 resistant (250 ng/ml for HCT-16 and 500 ng/ml for Colo-205A and Colo-320) colonies were selected (Singh et al., 1994b).

Figure 2C:
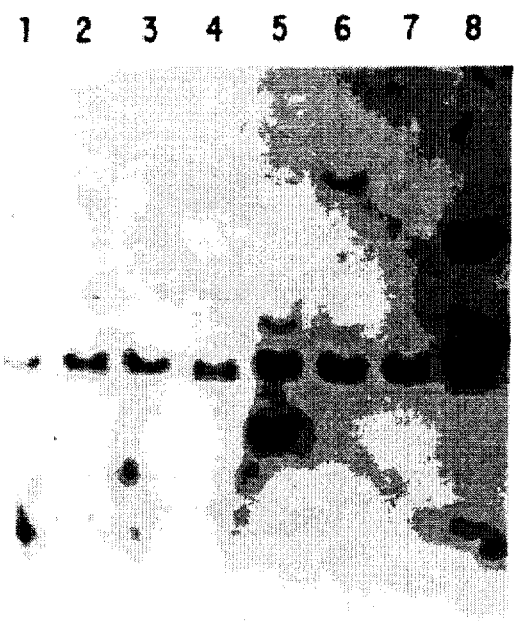
Figure 2D:
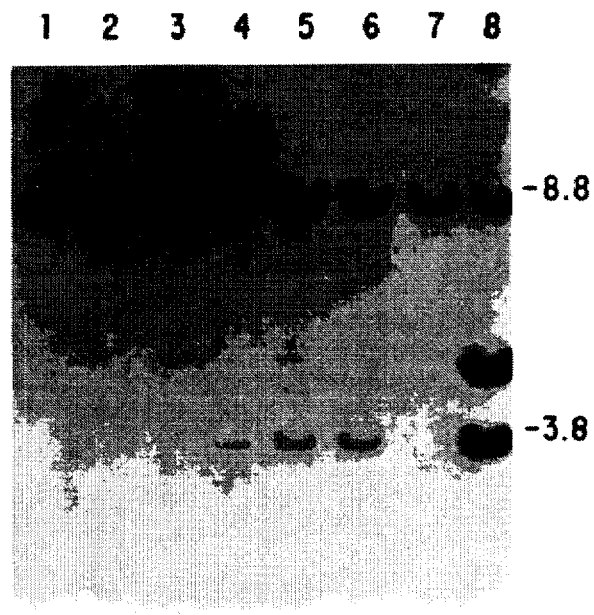

FIG. 2C and FIG. 2D: DNA was isolated from HCT-116 and Colo-320 cells transfected with either the gastrin antisense vector LNC-G-AS DNA (AS) or control (C) vector DNA.

Figure 3A:
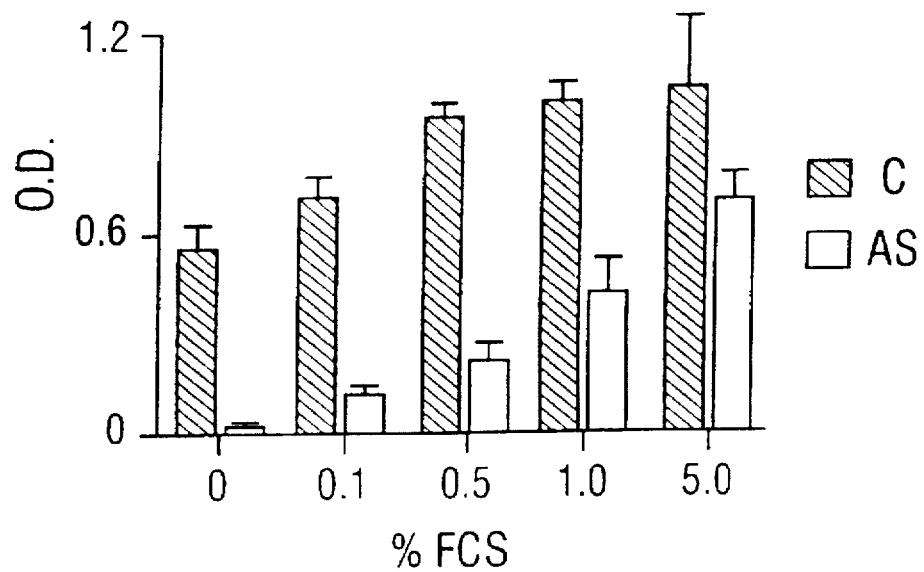
Figure 3B:
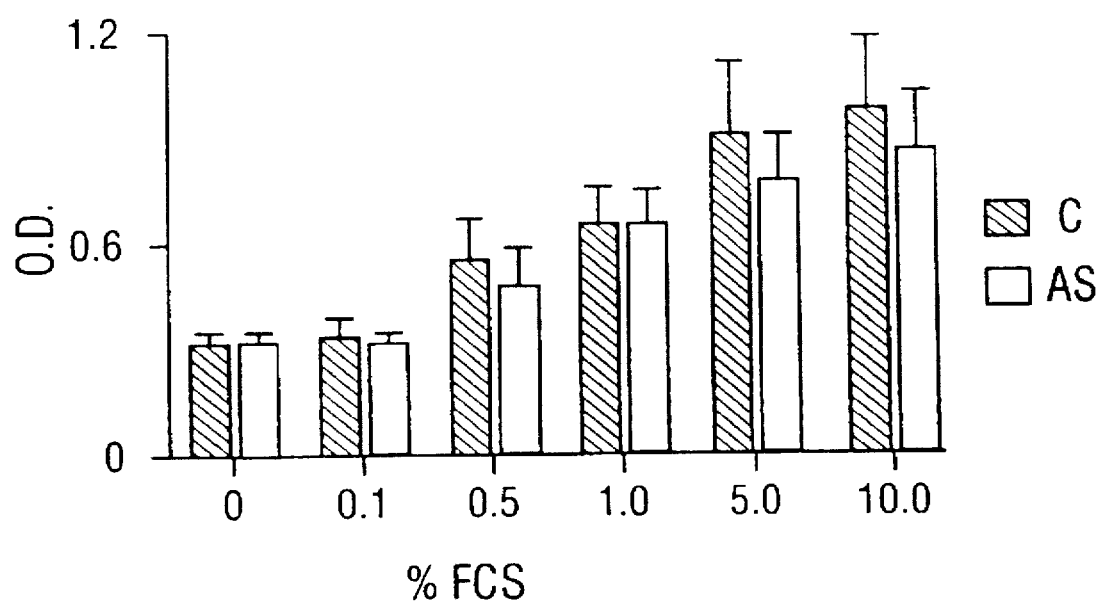

FIG. 3: The C and AS clones were plated at equal concentrations (6000/well) in 96-well plates. At the end of 7 days of growth in normal growth medium containing 0 to 10% FCS, the total number of viable cells was determined by an MTT assay (Guo cet al., 1990). The optical density (O.D.) of the Rx products was read at 540 nm by a microplate reader (Molecular Devices). Each bar represents mean ±SEM of 18 observations from 3 separate clones and is representative of 3–4 similar experiments. =p<0.05 vs the respective control values.

DETAILED DESCRIPTION OF THE PREFERRED EMBODIMENTS

Colorectal cancers are a major cause of cancer related death in the U.S. There seems to be very little effective therapy for patients expressing such cancers other than dramatic surgery. The genetic events leading to the development of colorectal cancer have been studied. However an understanding of molecular genetics of carcinogenesis, has not led to preventative or therapeutic measures. Advances in molecular genetics will lead to better risk assessment and early diagnosis but colorectal cancers will remain a deadly disease for a majority of patients due to the lack of an adjuvant therapy.

Ar least some colon cancers express gastrin and it is possible that gastrin plays a role in the initiation of colon tumors. However, the field is littered with conflicting reports as to the proliferative effects of gastrin and it processing intermediates in the development of colorectal cancers. There are, for example, reports suggesting that gastrin gene products are not completely processed by colon cancers. The processing intermediates of gastrin are thought to have a marked cell proliferating effect.

Other investigators have show gastrin does not stimulate the growth in all colon cancer cells. Thus there appears to be conflicting data on whether or not gastrin is involved in pathogenesis and the progression of colon cancer. Despite the conflicting data in this area. The present inventors contemplated that decreasing the gastrin expression may be therapeutically effective in diminishing the growth and/or inhibition of colon cancers.

Although there are antibodies available against gastrin, they are non-specific and cross react with cholecystokinin. Furthermore, antibodies are not available against all precursor forms of gastrin. Even if an antibody that was specific for all forms of gastrin was available, the large amounts of such an antibody that would be required to combat the effects of the gastrin gene products would make its therapeutic use impractical. In addition, therapeutic antibodies are often antigenic themselves.

The present inventors thus present an alternative that can be used for prophylaxis or treatment to inhibit growth of colon cancer cells.

1. Gastrin

Gastrin is a peptide hormone produced by the G-cells of the gastric antrum. It controls acid secretion by the stomach and is believed to regulate growth of the normal intestinal mucosa. However, recently another role for this peptide has emerged. It has been shown by the present inventors and others in the field that gastrin expression occurs in cancer cell lines. A possible role of gastrin as an autocrine growth factor for colon cancers is clearly different from its endocrine role as an acid secretion regulator and gastrointestinal muscosal growth regulator.

Many colon cancer cells express and secrete gastrin gene products (Dai et al., 1992; Kochman et al., 1992; Finley et al., 1993; Van Solinge et al., 1993; Xu et al., 1994; Sinlgh et al., 1994a; Hoosein et al., 1988; Hoosein et al., 1990) and bind gastrin-like like peptides (Singh et al., 1986; Singl et al., 1987; Weinstock and Baldwin, 1988; Watson and Steele, 1994; Upp et al., 1989; Singh et al., 1985) it is possible that gastrin-like like peptides serve as autocrine factors for colon cancers. In support of this, it is suggested that desensitization/internalization of gastrin receptors in response to endogenous gastrins may have rendered majority of the colon cancer cells refractory (non-responsive) to exogenous gastrins in previous studies. Similarly in previous reports gastrin antibodies were either reported to inhibit (Hoosein et al. 1988; Hoosein et al., 1990) on the growth of colon cancer cell lines in vitro. However, we now know that gastrin gene products are for the most part incompletely processed by colon cancers and processing intermediates (gly-gastrins and pro-gastrins) are the major forms expressed (Dai et al., 1992; Kochman et al., 1992; Van Solinge et al. 1993; Singh et al., 1994a; Ciccotosto et al., 1995). While in the past C-terminal amidation of gastrin-like peptides was considered a pre-requisite for measuring biological effects, it has been reported that non-amidated gastrins (especially gly-oastrins) exert proliferative effects on pancreatic cancer cells (Seva et al. 1994), fibroblasts, intestinal cells and colon cancer cells (Dai et al., 1992; Singh et al., 1994a; Baldwin, 1995; Singh et al., 1995).

Throughout the specification the term "gastrin gene product" is used; as used herein it refers to the product of the full gastrin encoding polynucleotide or any intermediates that may arise from the translation of the gastrin gene. "Processing intermediates" of gastrin are those peptides that may be derived through post translational modification of the gastrin gene, these include but are not limited to preprogastrin, progastrin (SEQ. ID NO: 7), amidated gastrins (SEQ. ID NO: 8 and SEQ ID:NO 9), gly-gastrin (SEQ. ID NO: 10) cryptogastrin (SEQ. ID NO: 11) and gastrin (SEQ ID NO: 12) itself.

In certain embodiments of the present invention it should be possible to inhibit the growth ot colon cancer cells by presenting to the cells antibodies derived against receptors of gastrin gene products. Another aspect of gastrini-stimulated colon cancer cell inhibition may involve antagonists of gastrin that would result in the inhibition of gastrin action.

The nucleic acid and corresponding amino acid sequences of human gastrin has been elucidated (SEQ ID NO: 1and SEQ IS NO: 2, respectively)

2. Antisense

Antisense constructs may be designed to bind to the promoter and other control regions, exons, introns or even exon-intron boundaries of a gene. The most effective antisense contructs include regions complementary to intron/ exon splice junctions. One preferred embodiment includes an antisense construct with complementary to regions within 50-200 bases of an intron-exon splice junction. It has been observed that some exon sequences can be included in the construct without seriously affecting the target selectivity thereof. The amount of exonic material included will vary, depending on the particular exon and introit sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are con- templated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genlomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

A preferred antisense sequence of the present invention is the complement to SEQ ID NO: 1, which is the antisense sequence of the gastrin cDNA.

3. In Vivo Delivery and Treatment Protocols (a) Adenovirus

One of the preferred methods for in vivo delivery involves the use of an adenovirus expression vector. "Adenovirus expression vector" is meant to include those constructs containing adenovirus sequences sufficient to support packaging of the construct and to express an antisense polynucleotide that has been cloned therein. In this context expression does not require that the gene product be synthesized.

The expression vector comprises a genetically engineered form of adenovirus. Knowledge of the genetic organization or adenovirus, a 36 kB, linear double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulations high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Relian, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system in is an alternative approach for the production of recombinant adenovirus.

Generation and propagation of adenovirus vectors, which are replication deficient, depend on a unique helper cell line, designated 293, which was transformed from human embryonic kidney cells by Ad5 DNA fragments and constitutively expresses E1proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Grahaam and Prevec, 1991).

In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1and E3regions, the maximum capacity of the current adenovirus vector is under 7.5 kB, or about 15% of the total length of the vector. More than 80% of the adenovirus viral Tenome remains in the vector backbone and is the source of vector-borne cytotoxicity.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g. Vero cells or other monkey embryonic mesenichymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 L siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 gal) is employed as follows. A cell inoculum, resuspended in 5 ml of medium, is added to the carrier (50 ml) in a 250 ml Erlenmeyer flask and left stationary, with occasional agitation, for 1to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, followingi which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, it has historically been used for most constructions employing adenovirus as a vector and it is non-oncogenic.

As stated above, a typical vector is replication defective and will not have an adenovirus E1region. Thus, it will be most convenient to introduce the polynucleotide encoding the gene of interest a the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cel line or helper virus complements the E4 defect.

Adenovirus is easy to grow and manipulate and exhibits broad host range in nitric and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirtis (Couch et al., 1963; Top et al., 1971), demonstrating their safety and therapeutic potential as in vivo gene transfer vectors.

Adenovirus vectors have been used in eukaryotic gene expression (Levrero et al., 1991; Gomnez-Foix et al., 1992) and vaccine development (Grunhaus and Horwitz, 1992; Graham and Prevec, 1992). Recently, animal studies suggested that recombinant adenovirus can be used for gene therapy (Stratford-Perricaudet and Perricaudet, 1 991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

(b) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences ale present at the 5' and 3' ends of the viral genome. These contain strong promoter and enhancer sequences and are also required lor integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, poll and env genes but without the LTR and packaging components is constructed (Mann et al., 1983). When a recombinant plasmid containing a human cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann el at., 1983). The media containing the recombinant retroviruses is then collected, optionally concentrated, and used for gene transfer. Retroviral vectors are able to infect a broad variety of cell types. However, integration and stable expression require the division of host cells (Paskind et cit., 1975).

A novel approach designed to allow specific targeting of retrovirus vectors was recently developed based on the chemical modification of a retroviris by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking, genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

(c) Other Viral Vectors as Expression Constructs

Other viral vectors may be employed as expression constructs in the present invention. Vectors derived from viruses such as vaccinia virus (Riddgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

(d) Non-viral Vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987, Rippe et al., 1990) DEAE-dextran (Gopal, 1985), electroporation (Tur-Kaspa et al., 1986, Potter et al., 1984), direct microinjection (Harland and Weintraub, 1985), DNA-loaded liposomes (Nicolau and Sene, 1982, Fraley et al., 1979) and lipofectamine-DNA complexes, cell sonication (Fechheimer et al., 1 987), gene bombardment using high velocity microprojectiles (Yang, et al., 1990), and receptor-mediated transfection (Wu and Wu, 1987, Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, I HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gyene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoproteini, which recognizes the same receptor as ASOR, has been used as a gene delivery vehicle (Ferkol et al., 1993: Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung epithelial or tumor cells, by any number of receptor ligand systems with or without liposomes. For example, epidermal growth factor (EGF) receptor may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

(e) Pharmaceutical Compositions

Where clinical applications are contemplated, it will be necessary to prepare a pharmaceutical compositions—either gene delivery vectors or engineered cells—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable canier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agyents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms.

The expression vectors and delivery vehicles of the present invention may include classic pharmaceutical preparations. Administration of these compositions according to the present invention will be via any common route so long as tile target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors and cells of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non--aqueous solvents are propylene (lycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well know parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5. Kits

All the essential materials and reagents required for inhibiting tumor cell proliferation may be assembled together in a kit. This generally will comprise selected expression vectors. Also included may be various media for replication of the expression vectors and host cells for such replication. Such kits will comprise distinct containers for each individual reagent.

When the components of the kit are provided in one or more liquid solutions, the liquid solution preferably is an aqueous solution, with a sterile aqueous solution being particularly preferred. For in vivo use, the expression vector may be formulated into a pharmaceutically acceptable syringeable composition. In this case, the container means may itself be an inhalant, syringe, pipette, eye dropper, or other such like apparatus, from which the formulation may be applied to an infected area of the body, such as the colon, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means.

The kits of the invention may also include an instruction sheet defining administration of the antisense gastrin-expression vector construct.

A gastrin gene as used herein will be any contiguous segment of the polynucleotide of SEQ ID NO: 1. This of course will include but is not limited to the polynucleotide sequences for preprogastrin, progastrin (SEQ. ID NO: 7), amidated gastrins (SEQ. ID NO: 8 and SEQ ID:NO 9), gly-gastrin (SEQ. ID NO: 10) cryptogastrin (SEQ. ID NO: 11) and gastrin (SEQ ID NO: 12) itself.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/ administration or placement of the ultimate complex composition within the body of an animal. Such an instrument may be an inhalant, syringe, pipette, forceps, measured spoon, eye dropper or any such medically approved delivery vehicle.

EXAMPLE I

Figure 1:
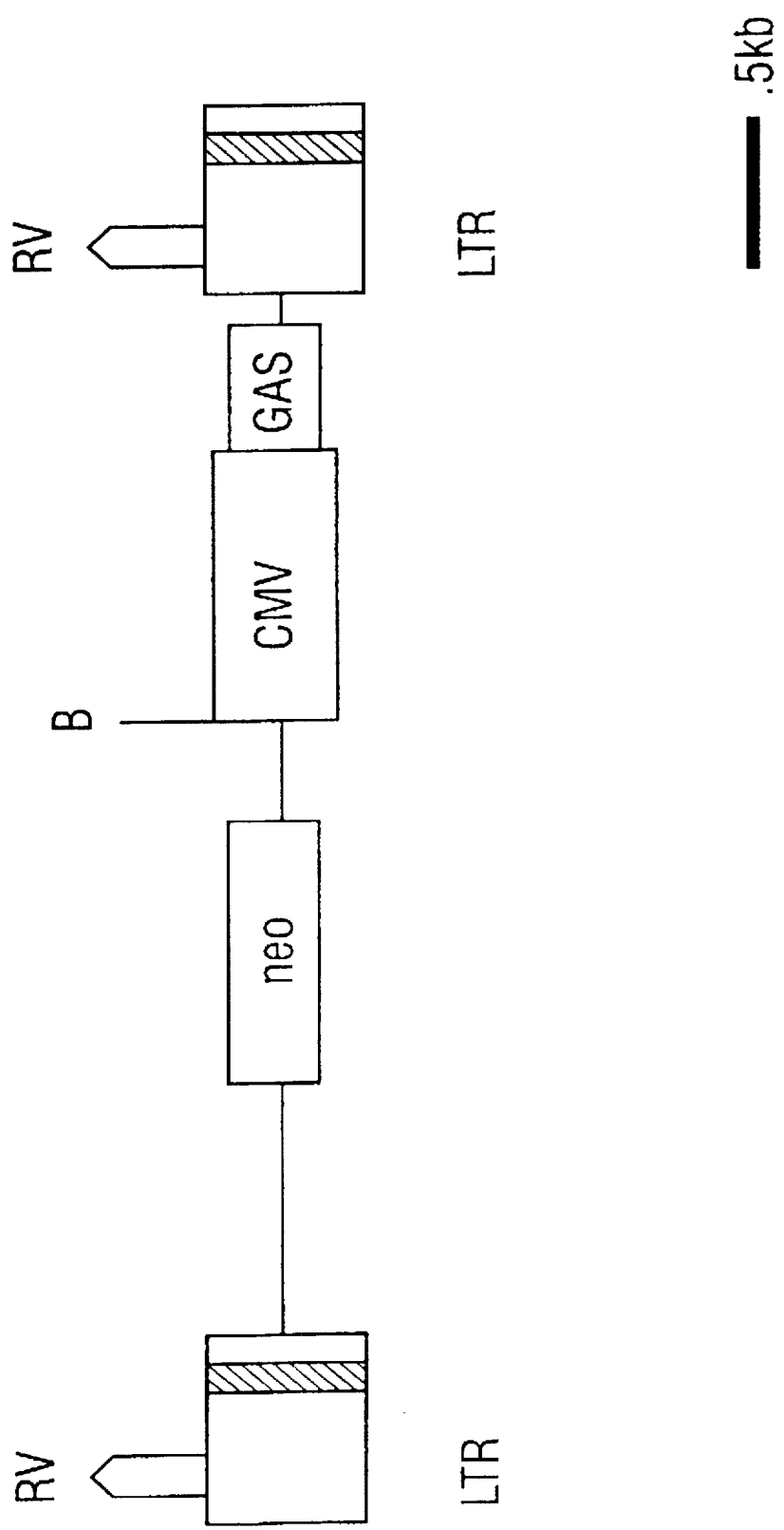
FIG. 1. Retroviral vector (LNCX, a kind gift from Dr. Dusty Miller, Fred Hutchinson Cancer Research Center, Seattle) containing the gastrin cDNA in the anti-sense orientation (G-AS) and under the transcription control of the cytomegalovirus (CMV) promoter is shown.

Expression of Antisense Gastrin cDNA into Colo-205A, Colo-320 and HCT-116 Colon Cancer Cell Lines A full length human gastrin cDNA was introduced in the antisense direction (GAS) into a retroviral vector (LNCX) (Miller et al., 1993), and the recombinant vector (LNC-G-AS) (FIG. 1) was confirmed using DNA sequence analysis. The long terminal repeat (LTR) sequences, the neomycin phosphotransferase gene (neo) and restriction endonuclease sites utilized in the analysis in FIG. 2C are indicated. The retroviral vector is propagated in bacteria using a 2.3 kb vector DNA sequence derived from pBR322. B, BamHI; RV, EcoRV.

Three representative human colon cancer cell lines were selected based on their relative levels of gastrin MRNA expression (FIG. 2A) and transfected with either the control (LNCX vector) DNA (C) or the anti-sense (LNC-G-AS) vector DNA (AS). Total cellular RNA was analyzed by a competitive RT-PCR method for measuring relative concentrations of gastrin mRNA/cell (Xu et al., 1994; Singh et al., 1994a). The Colo-205A, Colo-320 and HCT-16 cell lines expressed<0.5,–1–2 and 2–4 copies/cell. Since Colo-205A cells expressed negligible amounts of gastrin mRNA, this cell line served as a negative control.

The C and AS clones, numbered sequentially were expanded in vitro using Mccoy's 5A (HCT-116) and RPMI-1640 (Colo-205A, Colo-320) growth medium (Gibco) in the presence of 10% fetal calf serum (FCS) (Irvine Scientific). Total RNA was isolated (Narayan et al., 1992b) and analyzed for expression of AS gastrin mRNA transcripts using a sense primer derived from the retroviral vector, LNCX (CCTGGAGACGCCATCCACGCT; SEQ ID NO: 5) (5' to the G-AS insert) and an antisense primer ($HG_2$) from the G-AS insert (GTGTATGTGCTGATCTTTGCACTG; SEQ ID NO: 6). A DNA fragment, consistent with the predicted size (482 bp), was present in all of the AS clones analyzed. None of the C clones were positive for the AS gastrin mRNA. Representative data from some of the C and AS clones from the 3 cell lines is presented. Lanes 1–8 for HCT-116=Mw markers, $C_2$, AS $_1$, $AS_2$, $AS_3$, $AS_4$, $C_3$ and Mw markers, respectively. Lanes 1–7 for Colo-205A=Mw markers, $C_1$, $C_3$, $C_4$, $AS_1$, $AS_2$, and $AS_3$, respectively. Lanes 1–5 for Colo-320 =Mw markers, $C_1$, $C_2$, $AS_2$ and $AS_3$, respectively.

The cell lines were transfected with either the C or the AS vectors and G418 resistant colonies selected as described (Singh et al., 1994b). The clones were expanded in growth medium containing 10% FCS under constant drug selection. Of the five Colo-320-AS clones only one clone ($AS_2$) produced a sufficient number of cells to permit partial characterization and analysis.

The Colo-320-$AS_2$ clone was analyzed using Southern hybridization and RT-PCR to ascertain the insertion and the expression of the LNC-G-AS vector (FIG. 2B and FIG. 2C). Southern analysis confirmed the presence of one or more integrated copies of the LNC-G-AS proviral DNA in each of the LNC-G-AS transfectants (FIG. 2C). Genomic DNA (10 µg) was digested with either BamHI (FIG. 2C) or EcoRV (FIG. 2D) using conditions recommended by the manufacturer (New England Biolabs) and analyzed by electrophoresis on 0.75% agarose gels as described (Wood et al. 1994).

The results from EcoRV digests (FIG. 2D) suggest that all of the integrated proviral DNAs in HCT-116-AS clones have not undergone a rearrangement of the transfected retrovirus DNA. Hybridization analysis was performed using a $^{32}P$-dCTP labeled probe representing the entire open reading frame of the gastrin cDNA. Lane 1, HCT-116-$C_2$; Lane 2, HCT-116-$C_3$; Lane 3, HCT-116; Lane 4, HCT-116-$AS_2$; Lane 5, HCT-116-$AS_3$; Lane 6, HCT-116-$AS_6$; Lane 7, Colo-320-$C_3$; Lane 8, Colo-320-$AS_2$.

The Colo-320-AS clone (FIG. 2D lane 8) contains at least two integrated copies and one of these has undergone rearrangement. The endogenous gastrin gene is also detected in each of the DNA digests (4.9 kb, BamHI; 8.8 kb, EcoRV).

Since the expression of gastrin AS RNA produced such a dramatic effect upon the proliferation of Colo-320 cells, it suggested for the first time that gastrin mRNA expression may indeed be critical to the growth of some colon cancer cell lines. Besides exhibiting an almost complete growth arrest, the size of the Colo-3 20-AS cells was significantly increased (10–20 fold) compared to that of the control clones.

The Colo-320-AS clones demonstrated distinct morphological differences under the electron microscope (EM) compared to control clones. The Colo-320-AS cells were multi-nucleated with euchromatin and a high concentration of mitochondria, while the Colo-320-C cells contained the expected heterochromatin and few mitochondria. The Colo-320-AS cells, while clearly growth arrested, appeared to be metabolically active and excluded Trypan blue dye. These distinct morphological differences between the Colo-320-C and -AS clones may provide the first clues of possible intracellular mechanisms that may be mediating the mitogenic effects of gastrin gene products in colon cancer cells.

EXAMPLE II

Anti-Proliferative Effects of Antisense Gastrin RNA in HCT-116 Cells

The anti-proliferative effects of expressing gastrin AS RNA in the HCT-116-AS cells were also analyzed. The in vitio proliferative rate of the HCT116-C and AS clones was compared using an MTT assay (Guo et al., 1990). The proliferation of the HCT-116-AS clones in serum free medium (SFM) was 5% of that measured for HCT-116-C clones in SFM (FIG. 3). The proliferation of the HCT-116-AS clones increased in response to increasing concentrations of FCS, but remained lower than that of HCT-116-C clones at equivalent concentrations of FCS (FIG. 3).

A soft agar clonogenic assay (Macpherson and Montagnier, 1964) was used in order to determine the in vitro tumoringenic potential of the cells. The number of colonies formed by HCT-116-AS cells in increasing concentrations of FCS, remained only 0–5% compared to that formed by the HCT-116-C clones. The in vitro tumorigenic potential for the C and AS clones of HCT-116 and Colo-205A cells was determined from a soft agar clonogenic assay (Macpherson and Montagnier, 1964). The cells were seeded at equal concentrations (8000/well) in 6-well culture plates in 0.3% agar in regular growth medium containing 0.1–10% FCS. The total number of colonies/well were<1–5% in wells seeded with HCT-116-AS clones (at all concentrations of FCS) compared to wells seeded with HCT-116-C clones. Representative wells demonstrating total number of colonies formed by HCT-116-$AS_2$ and HCT-116-$C_2$ clones after 14 days of seeding in 1% FCS are shown.

The size of the colonies formed by HCT-116-AS vs HCT-116-C clones was also vastly different. The size and number of colonies formed by the Colo-205A-AS and -C clones, was similar in all cases. Thus while the proliferative potential of the HCT-116-AS clones (especially in 10% FCS) was not as drastically effected as that of the Colo-320-S clones, the in vitro tumorigenic potential of the HCT-116-AS clones (even in 10% FCS) was significantly suppressed compared to that of the HCT-116-C and Colo-320-C clones.

Morphologically, the HCT-116-AS clones also appeared to be significantly different compared to the HCT-116-C clones. HCT-116-AS cells were -2–4 fold larger in size, contained euchromatin, prominent nucleolus and signs of microvilli formation; HCT-116-C cells appeared to be normal colon cancer cells with typical heterochromatin.

EXAMPLE III

In Vivo Anti-Tumorioenic Effects of Expression of Gastrin Antisense RNA

To examine the in vivo anti-tumoricenic effects of expression of gastrin AS RNA nude mice tumor formation assays were conducted. Cells from the HCT-116-AS and -C clones were inoculated into nude mice (Narayan et al., 1992a; Singh et al., 1993). The in mice were palpated for tumors from Day 10.

The HCT-116-AS and C clones, enumerated in vitro in 1% FCS were inoculated contralaterally at equal concentrations (0.1–0.5×10$^7$ cells/0.2 ml HBSS) in female nude (athymic) mice, age 2 months (Life Sciences, St. Petersburg, Fla.) following published procedures (Singh et al., 1986; Singh et al., 1987).

The mice were euthanized between Days 21–45 and tumors, free of host tissues, removed (Singh et al., 1986; Singh et al., 1987) and tumor weights noted (Table 1). Each data point represents mean ±SD of tumor weights from 2–3 mice inoculated with the indicated AS and control clones growing contralaterally in mice; range of values measured is given in parenthesis. Either no or significantly smaller tumors were obtained from the mice inoculated with HCT-116-AS clones (Table 1); tumors were palatable as early as Day 12 in the mice inoculated with the HCT-116-C clones. A well formed tumor was removed from every HCT-116-C inoculation site at the time of euthanasia, and confirmed for vector DNA.

The marked suppression of turnorigenesis of HCT-116-AS clones in vivo once again suggests that gastrin gene products may play a critical role in the growth and tumorigenesis of human colon cancer cells that normally are express significant concentrations of gastrin mRNA.

TABLE I

Tumorigenicity of HCT-116-AS and -C clones in vivo in nude mice

| Mice # | Right Side Clone # | Right Side Weight (mgs) | Left Side Clone # | Left Side Weight (mgs) | Day of Euthanasia (Post Inoculation) |
|---|---|---|---|---|---|
| 1, 2, 3 | $C_2$ | 639 ± 220 (400–850) | $AS_4$ | 43.3 ± 75 (0.0–130) | 37 |
| 4, 5, 6 | $C_3$ | 534 ± 127 (397–650) | $AS_3$ | 48.0 ± 59 (0.0–114) | 37 |
| 7, 8, 9 | $C_8$ | 217 ± 89 (123–300) | $AS_{10}$ | 1.5 ± 2 (0.0–3.0) | 22 |
| 10, 11 | $C_7$ | 417 ± 6 (413–422) | $AS_9$ | 0.0 ± 0.0 (0.0–0.0) | 22 |

TABLE 2

Relative concentration of pro-gastrin and gly-gastrin in cellular extracts and conditioned media of HCT-116-C and -AS clones.

| Cell Line/clone | FCS Stimulation 0.1% Pro-G | 0.1% G-G | 1.0% Pro-G | 1.0% G-G |
|---|---|---|---|---|
| | Cellular Extract (CE) Samples | | | |
| HCT-116-C | 44.1 ± 2.0 (100.0) | 22.6 ± 8.2 (100.0) | 64.8 ± 9.3 (100.0) | 23.6 ± 3.9 (100.0) |
| HCT-116-AS | 15.5 ± 1.6 (35.1%) | 8.8 ± 0.3 (38.9%) | 25.0 ± 0 (38.5%) | 14.4 ± 0.7 (61.0%) |
| | Conditioned Media (CM) Samples | | | |
| HCT-116-C | 26.7 ± 3.0 | 22.3 ± 1.5 | 57.0 | 25.1 ± 3.6 |
| HCT-116-AS | <1.0 | <1.0 | <1.0 | <1.0 |

EXAMPLE IV

Gastrin-like Peptides in Colon Cancer Cells

The concentrations of amidated gastrin and processing intermediates of gastrin (pro-gastrin and gly-gastrin) (Varro et al., 1995; Nemeth et cl., 1992a), in the cellular extracts (CE) and conditioned media (CM) of the HCT-116-AS and -C cells were also measured.

The concentration of gastrin-like peptides in the CM samples of AS clones was <1% compared to that in the CM of C clones (Table 2). Two representative HCT-116-AS ($AS_2$, $AS_3$) and two representative HCT-116-C ($C_2$, $C_3$) clones were selected for analysis of gastrin-like peptides by RIA. The clones were expanded in vitro in 0.1 and 1% FCS. Cells were washed in PBS, scraped with a rubber policeman, counted with a Coulter counter, and an equivalent number of cells ($1\times10^8$) suspended in 1 ml distilled water, boiled for 5 min, concentrated and de-salted using 1000× cut-off amicon membranes. These samples were labeled CE. An equivalent number of cells in duplicate 75 cm² flasks were processed for CM collection by our published procedures (Singh et al., 1994c) and the CM samples concentrated using the amicon concentrators. The CE and CM samples were analyzed for pro-gastrin, gly-gastrin, and amidated gastrin using specific antibodies L-289, L376 and L2, respectively, by RIA, as published previously (Varro et al., 1995; Nemeth et al., 1992a). Each data point represents fmoles/$10^7$ cells and is the mean ±SD of 4 separate observations from 2 separate clones. The mean values for AS clones are also presented as a percentage of the respective control values (arbitrarily assigned a 100% value).

The concentration of pro-gastrins and gly-gastrins was significantly reduced in the CE samples of AS vs C clones. In contrast, a difference in the level of pp60src-kinase protein (an unrelated protein expressed by colonn cancer cells, Singh et al., 1994c and Singh et al., 1994d), was not observed in the CM samples of AS and C cells.

These results support the conclusion that the anti-proliferative effects measured as a result of AS gastrin RNA expression were specific and due to a significant reduction in the concentration of gastrin-like peptides.

The proliferation and tumorigenic potential of the Colo-205A-AS and -C clones was similar (FIG. 3), suggesting that the anti-proliferative and anti-tumorigenic effects of anti-sense expression of gastrin RNA were specific to colon cancer cells expressing significant concentrations of endogenous gastrin mRNA (Colo-320 and HCT-16 cells). No non-specific effects were measured on either the morphology, tumorigenciicity, or proliferation (FIG. 3) of Colo-205A cells expressing negligible concentrations of endogenous gastrin mRNA. The Colo-205A-AS clones expressed similar concentrations of AS gastrin RNA as the HCT-116-AS and the Colo-320-AS clones (FIG. 2B), further confirming the specificity of the effects of anti-sense gastrin RNA expression on only the gastrin expressing colon cancer cell lines.

Previous studies with antibodies suggested that gastrins may function as autocrine growth factors for colon cancers (Hoosein et al., 1988; Hoosein et al., 1990). The present inventors' studies confirm that gastrin gene products may be novel autocrine growth factors for human colon cancer cell lines that are expressing significant concentrations of gastrin mRNA. The present inventors have demonstrated significant inhibition in the growth of Colo-320 cells with gastrin antisense oligonucleotides (20–23 mer).

The present inventors results further demonstrate that expression of the gastrin AS RNA via the retroviral construct used will effective in suppressing the growth of human colon cancers expressing gastrin mRNA.

Based on current knowledge that perhaps>60–80% of human colon cancers express gastrin mRNA, delivery of gastrin AS RNA expression vectors to a tumor site and transfection of the tumor cell will significantly suppress the growth of gastrin expressing colon cancers. Tumor cells not expressing gastrin but stimulated by gastrin produced by other cells would also be suppressed by antisense inhibition of gastrin production by other cells.

Colon cancers expressing a minimal concentration of gastrin mRNA are not as likely to respond to the anti-tumorigenic effects of gastrin AS RNA expression and may perhaps represent a sub-set of tumors that have developed autocrine mechanisms independent of gastrin gene products, unless their are dependent on gastrin produced by other cells that are, infact, transformed.

EXAMPLE V

Clinical Trials of the Use Antisense Gastrin in Treating Colorectal Cancer

This example is concerned with the development of human treatment protocols using, the antisense gastrin, Antisense gastrin treatment will be of use in the clinical treatment of colon cancers in which transformed or cancerous cells play a role. Such treatment will be particularly useful tools in anti-tumor therapy, for example, in treating, patients with colorectal cancers that are hormone dependent and mediated by gastrin or gastrin-like peptide expression.

The various elements of conducting a clinical trial, including patient treatment and monitoring, are known to those of skill in the art in light of the present disclosure. The following information is being presented as a general guideline for use in establishing antisense gastrin therapy in clinical trials.

Patients with advanced, colorectal cancers are appropriately selected for clinical study. Measurable disease is not required, however the patient preferably has easily accessible pleural effusion and/or ascites. Further the patients most preferably carry tumors that express gastrin or its processing intermediates. In an exemplary clinical protocol, patients may undergo placement of a Tenckhoff catheter, or other suitable device, into the site of the tumor. Typically, bone marrow function, platelet count and renal function are measured to determine the baseline cellularity.

The patient receives first a treatment of $10^8$ infectious particles of adenovirus-antisense gastrin construct, diluted in sterile phosphate buffered saline, via endoscopic intratumoral injections (total volume 1 ml). Every three days the patient receives an identical treatment until a total of six treatments have been given. Other levels of construct dosages or administration protocols may be used to optimize desired results.

Three days after the sixth treatment, the tumor is examined to affirm that it has decreased in size. Histological examinations should show considerable cell fragmentation at the tumor margin. Levels of gastrin production should have decreased markedly. A second course of six treatments is undertaken following which the tumor is further decreased in size and is undergoing necrosis. The patient continues to receive weekly treatments for three months or other lengths of time which the tumor should no longer be evident.

Of course, the above-described treatment regimes may be altered in accordance with the knowledge gained from clinical trials that may be conducted as is routinely practiced by those of skill in the art. Those of skill in the art will be able to take the information disclosed in this specification and optimize treatment regimes based on the clinical trials such as those described in this specification.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and plhysiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baichwal & Sugden, "Vectors for gene transfer derived from animal DNA viruses:
Transient and stable expression of transferred genes." In: *Gene transfer*, Kucherlapati (ed.), New York: Plenum Press, pp. 117–148, 1986.

Baldwin and Zhang, *Cancer Res.*, 52:2261, 1992.

Baldwin, *FEBS Lett.*, 359:97, 1995.

Benvenisty & Neshif. "Direction introduction of genes into rats and expression of the genes." *Proc. Nat. Acad. Sci. USA*, 83:9551-9555, 1986.

Chang et al., "Foreign gene delivery and expression in hepatocytes using a hepatitis B virus vector." *Hepatology*, 14:124A, 1991.

Chen & Okayama, "High-efficiency transfection of mammalian cells by plasmid DNA," *Mol. Cell Biol.*, 7:2745-2752, 1987.

Ciccotosto et al., *Gastroenterology*, 109:1142, 1995.

Coffin, "Retroviridae and their replication." In: *Virology*. Fields et al. (eds.), New York: Raven Press, pp. 1437-1500, 1990.

Couch et al., "Immunization with types 4 and 7 adenovirus by selective infection of the intestinal tract," *Am. Rev. Resp. Dis.*, 88:394-403, 1963.

Coupar et al., "A general method for the construction of recombinant vaccinia virus expressing multiple foreign genes." *Gene*, 68:1-10, 1988.

Dai et al., *Gastroenterology*, 102:352, 1992.

Dubensky et al., "Direct transfection of viral and plasmid DNA into the liver or spleen of mice," *Proc. Nat. Acad. Sci. USA*, 81:7529-7533, 1984.

Fearon and Vogelstein, *Cell*, 61:759, 1990.

Fechheimer et al., "Transfection of mammalian cells with plasmid DNA by scrape loading and sonication loading." *Proc. Natl. Acad. Sci. USA*, 84:8463-8467, 1987.

Finley et al., *Cancer Res.*, 53:2919, 1993.

Fraley et al., "Entrapment of a bacterial plasmid in phospholipid vesicles: Potential for gene transfer," *Proc. Natl. Acad. Sci. USA*, 76:3348-3352, 1979.

Friedmann, "Progress toward human gene therapy," *Science*, 244:1275-1281, 1989.

Ghosh & Bachhawat, "Targeting of liposomes to hepatocytes," In: *Liver diseases, targeted diagnosis and therapy using specific receptors and ligands*, Wu & Wu (eds.), New York: Marcel Dekker, pp. 87-104, 1991.

Ghosh-Choudhury et al., "Protein 1X, a minor component of the human adenovirus capsid, is essential for the packaging of full-length genomes," *EMBO. J.*, 6:1733-1739, 1987.

Gomez-Foix et al., "Adenovirus-mediated transfer of the muscle glycogen phosphoresce gene into hepatocytes confers altered regulation of glycogen," *J Biol. Chem.*, 267:25129-25134, 1992.

Gopal, "Gene transfer method for transient gene expression, stable transfection, and cotransfection of suspension cell cultures," *Mol Cell Biol.*, 5:1188-1190, 1985.

Graham & Prevec. "Adenovirus-based expression vectors and recombinant vaccines," *Biotechnology*, 20:363-390, 1992.

Graham & Van Der Eb, "A new technique for the assay of infectivity of human adenovirus 5 DNA," *Virology*, 52:456-467, 1973.

Graham et al., "Characteristics of a human cell line transformed by DNA from human adenovirus type 5," *J. Gen. Virol.*, 36:59-79, 1977.

Grunhaus & Horwitz, "Adenovirus as cloning vector," *Seminar in Virology*, 3:237-252, 1992.

Guo et al., *In Vitro Cell. Dev. Biol.*, 26:871, 1990.

Harland & Weintraub, "Translation of mammalian mRNA injected into Xenopus oocytes is specifically inhibited by antisense RNA," *J. Cell Biol.*, 101:1094-1099, 1985.

Hersdorffer et al., "Efficient gene transfer in live mice using a unique retroviral packaging line," *DNA Cell Biol.*, 9:713–723, 1990.

Herz & Gerard, "Adenovirus-mediated transfer of low density lipoproteini receptor gene acutely accelerates cholesterol clearance in normal mice.," *Proc. Ntil. Acad. Sci. USA* 90:2812–2816, 1993.

Hoosein et al., *Exp. Cell. Res.*, 186:15, 1990.

Hoosein et al., *Carncer Res.*, 48:7179, 1988.

Horwich et al., "Synthesis of hepadenovirus particles that contain replication-defective duck hepatitis B virus genomes in cultured HuH7 cells," *J Virol.*, 64:642–650, 1990.

Jones & Shenk, "Isolation of deletion and substitution mutants of adenovirus type 5," *Cell*, 13:181–188, 1978.

Kaneda et al., "Increased expression of DNA cointroduced with nuclear protein in adult rat liver," *Science*, 243:375–378, 1989.

Karlin et al. *Cancer Lett.*, 29:73. 1985.

Kato et al., "Expression of hepatitis B virus surface antigen in adult rat liver," *J. Biol. Chem.*, 266:3361–3364, 1991.

Klein et al., "High-velocity microprojeetiles for delivering nucleic acids into living cells," *Nature*, 327:70–73. 1987.

Kochman et al., *Biochem. Biophys. Res. Commun.*, 189:1165, 1992.

Lamote and Willems, *Regul. Pept.*, 20:1, 1988.

Le Gal La Salle et al., "An adenovirus vector for gene transfer into neurons and glia in the brain," *Science*, 259:988–990, 1993.

Levrero et al., "Defective and nondefective adenovirus vectors for expressing foreign genes in vitro and in vivo," *Gene*, 101: 195–202, 1991.

Macpherson and Montagnier, *Virology*, 23:291, 1964.

Mann et al., "Construction of a retrovirus packaging mutant and its use to produce helper-free defective retrovirus," *Cell*, 33:153–159, 1983.

Markowitz et al., "Construction and use of a safe and efficient amphotropic packlaging cell line," *Virology*, 167:400–406, 1988

Miller et al., *Methods Enzymol.* 217:581, 1993.

Montag et al., *Proc. Natl. Acad. Sci. U.S.A.*, 90:6696, 1993.

Narayan et al., *Cell Growth & Differ.* 3:111, 1992b.

Narayan et al., *Gastroenterology*, 103:1823 1992a.

Nemeth et al., *Eur. J. Clin. Invest.*, 22:638, 1992a.

Nemeth et cl., GUT, 34:90, 1992b.

Nicolas & Rubenstein, "Retroviral vectors," In: *Vectors: A survey of molecular cloning vectors and their uses*, Rodriguez & Denhardt (eds.), Stoneham: Butterworth, pp. 493–513, 1988.

Nicolau & Sene, "Liposome-mediated DNA transfer in eukaryotic cells," *Biochim. Biophys. Acta*, 721:185–190, 1982.

Nicolau et al., "Liposomes as carriers for in Vivo gene transfer and expression," *Methods Enzymvol.*, 149:157–176, 1987.

Parekh et. al., *Pattcreas*, 9:83, 1994.

Paskind et al., "Dependence of moloney murine leukemia virus production on cell growth," *Virology*, 67:242–248, 1975.

Perales et al., *Proc. Natl. Acad. Sci., USA*, 91:4086–4090, 1994.

Ragot et al., "Efficient adenovirus-mediated transfer of a human minidystrophin gene to skeletal muscle of mdx mice," *Nature*, 361:647–650, 1993.

Rehfeld and van Solinge, In. *Advances in Cancer Research*, Academic Press, New York, 63:295–346, 1994.

Renan, "Cancer genes: Current status, future prospects and applications in radiotherapy/oncology," *Radiother. Oncol.*, 19:197–218, 1990.

Ridgeway, "Mammalian expression vectors," In: *Vectors: A survey of molecular cloning vectors and their uses*, Rodriguez & Denhardt (eds.), Stoneham: Butterworth, pp. 467–92, 1988.

Rippe et al., "DNA-mediated gene transfer into adult rat hepatocytes in primary culture," *Mol. Cell Biol.*, 10:689–695, 1990.

Rosenfeld et al., "Adenovirus-mediated transfer of a recombinant $\alpha$1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium." *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Seva et al., *Science*, 265:410, 1994.

Singh et al., *Am. J. Physiol.*, 249:G761, 1985.

Singh et al., *Am. J. Physiol.*, 266:G459, 1994a.

Singh et al., *Am. J Physiol.*, 267:G608, 1994c.

Singh et al., *Am. J. Physiol.*, 267:G235, 1994d.

Singh et al., *Cancer J.*, 3 :28, 1990.

Singh et al., *Cancer Res.*, 46:1612, 1986.

Singh et al., *Cancer Res.*, 47:5000, 1987.

Singh et al., *Cancer Res.*, 54:6563, 1994b.

Singh et al., *J. Biol. Chem.*, 270:8429, 1995.

Singh et al., *J. Steroid Biochem. Mol. Biol.*, 46:49, 1993.

Smith and Solomon, Gastroenterology, 95:1541, 198F.

Steele Jr, *Cancer*, 74:1979, 1994.

Stratford-Perricaudet & Perricaudet p. 51–61, In: *Human Gene Transfer*, Cohen-Haguenauer & Boiron (eds.), Editions John Libbey Eurotext, France, 1991.

Stratford-Perricaudet et al., *Hum. Gene Ther.*, 1:241–256, 1990.

Sumiyosh: et al., *Cancer Res.*, 44:4276, 1984.

Temin, In: *Gene Transfer*, Kucherlapati (ed.), New York: Plenum Press, pp. 149–188. 1986.

Top et al., *J. infect . Dis.*, 124:155–160, 1971.

Tur-Kaspa et al., *Mol. Cell Biol.*, 6:716–718, 1986.

Upp Jr. et al., *Cancer Res.*, 49:488, 1989.

Van Solinge et al., *Gastroenterology*, 104:1099, 1993.

Varmus et al., *Cell*, 25:23–36, 1981.

Varro et al., *J. Clin. Invest.*, 95:1642, 1995.

Wagner et al., *Science*, 260:1510–1513, 1990.

Watson and Steele, In: *Gastrin receptors in GI tumors*, CRC Press, Boca Raton, Fla, pp 1–99 1994.

Weinstock and Baldwin, *Cancer Res.*, 48:932, 1988.

Williamson et al., *Cancer Res.*, 38:3212, 1978.

Wong et al., *Gene*, 10:87–94, 1980.

Wood et al., In: *Molecular Basis of inflammation*, J. Navarro, Ed., Raven Press, Heidelberg, p. 217, 1994.

Wu & Wu, *Biochemistry*, 27:887–892, 1988.

Wu & Wu, *J Biol. Chem.*, 262:4429–4432, 1987.

Wu & Wu, *Adv. Drug Delivery Rev.*, 12:159–167, 1993.

Xu et al., *Life Sci.*, 54:671, 1994.

Yang et al., *Proc. Natl. Acid. Sci. USA*, 87:9568–9572, 1990.

Zelenin et al., *FEBS Lett.*, 280:94–96, 1991.

What is claimed is:

1. An isolated genetic construct comprising an antisense polynucleotide sequence of SEQ ID NO:1 flanked by SEQ ID NO:3 at the 5' end, and by SEQ ID NO:4 at the 3' end, wherein transfection in vitro of gastrin-producing human colon cancer cells by a vector comprising said isolated genetic construct results in reduced expression of gastrin gene products.

2. The isolated genetic construct of claim 1 defined further as inhibiting the growth of human colon cancer cells.

3. The isolated genetic construct of claim 1 defined further as comprising a promotor.

4. The isolated genetic construct of claim 1 defined further as including a vector.

5. The isolated genetic construct of claim 1 defined further as comprising a viral vector.

6. The isolated genetic construct of claim 1 defined further as comprising a retroviral vector.

7. The isolated genetic construct of claim 1 defined further as comprising an adenoviral vector or an adeno-associated viral vector.

8. The isolated genetic construct of claim 1 defined further as including a promotor from CMV, LTR or SV40.

9. The isolated genetic construct of claim 1 defined further as including a segment within 50–200 bases of an intron/exon splice junction.

* * * * *

UNITED STATES PATENT AND TRADEMARK OFFICE
CERTIFICATE OF CORRECTION

PATENT NO.   :   5,786,213
DATED        :   July 28, 1998
INVENTOR(S)  :   Singh et al.

It is certified that error appears in the above-identified patent and that said Letters Patent is hereby corrected as shown below:

Title page, item [57], line 1, delete "is" and insert --methods-- therefor.

Signed and Sealed this

Twenty-ninth Day of September, 1998

Attest:

BRUCE LEHMAN

Attesting Officer          Commissioner of Patents and Trademarks